(12) United States Patent
Arkusz et al.

(10) Patent No.: US 9,271,825 B2
(45) Date of Patent: Mar. 1, 2016

(54) PULSATING STENT GRAFT

(76) Inventors: Mike Arkusz, Chandler, AZ (US); Tom Arkusz, Chandler, AZ (US)

(*) Notice: Subject to any disclaimer, the term of this patent is extended or adjusted under 35 U.S.C. 154(b) by 567 days.

(21) Appl. No.: 10/248,661

(22) Filed: Feb. 6, 2003

(65) Prior Publication Data

US 2005/0027346 A1 Feb. 3, 2005

(51) Int. Cl.
*A61F 2/06* (2013.01)
*A61F 2/07* (2013.01)

(52) U.S. Cl.
CPC ........... *A61F 2/07* (2013.01); *A61F 2230/0078* (2013.01)

(58) Field of Classification Search
CPC .......................... A61F 2/07; A61F 2230/0078
USPC ............... 623/1.15, 1.13, 1.3, 1.18, 1.17, 1.2, 623/1.21, 1.37, 23.64, 23.7, 1.31, 1.44, 623/1.49, 1.51; 600/36
IPC ......................................................... A61F 2/06
See application file for complete search history.

(56) References Cited

U.S. PATENT DOCUMENTS

| 5,104,402 | A | * | 4/1992 | Melbin | 623/1.37 |
| 5,282,847 | A | * | 2/1994 | Trescony et al. | 623/1.29 |
| 5,591,195 | A | * | 1/1997 | Taheri et al. | 623/1.11 |
| 6,048,362 | A | * | 4/2000 | Berg | 623/1.34 |
| 6,371,982 | B2 | * | 4/2002 | Berg et al. | 623/1.4 |
| 6,554,855 | B1 | * | 4/2003 | Dong | 623/1.13 |
| 6,579,307 | B2 | * | 6/2003 | Sarac | 623/1.13 |
| 6,814,754 | B2 | * | 11/2004 | Greenhalgh | 623/1.51 |
| 7,137,947 | B2 | * | 11/2006 | Sarac | 623/1.44 |
| 2003/0097172 | A1 | * | 5/2003 | Shalev et al. | 623/1.31 |
| 2008/0033501 | A1 | * | 2/2008 | Gross | 607/44 |

FOREIGN PATENT DOCUMENTS

WO 01/72239 * 10/2001
WO WO 0172239 * 10/2001

* cited by examiner

*Primary Examiner* — Julian W Woo

(57) ABSTRACT

A tubular vascular stent graft with passively pulsating section where the difference between the cross-sectional areas of the lumen under the systolic and diastolic pressures after the implantation is 10% or more. The pulsating stent graft accumulates blood during the systolic pressure wave thus lowering the peak value of the tugging force at the proximal attachment site.

1 Claim, 1 Drawing Sheet

PULSATING STENT GRAFT

BACKGROUND OF INVENTION

Tubular flexible grafts are currently a standard tool for repairing failures in the vascular system. During open surgical procedures such grafts are securely sewn onto the vessel in a manner that prevents detachment or leakage. Open surgical procedures however often carry substantial risk to the patient. In recent years a new technology has emerged which seeks to deliver grafts supported by stents through the use of catheter like devices introduced into the vascular system at a convenient location and then guided remotely to the site where the stent graft is implanted.

One of the more serious problems that the physicians using this technology have to cope with relates to the fact that the intraluminally implanted graft is less securely attached to the vessel wall and can therefore slip away from the intended location. Consequences of such slippage in the case of a large artery can be very serious. Various methods have been developed to counter this problem. Since trouble typically develops at the proximal attachment site, proximal ends of grafts have been equipped with hooks or uncovered stents, which after deployment extend beyond the treated area of the vessel to provide the necessary anchoring.

SUMMARY OF INVENTION

The present invention is a tubular vascular stent graft with a passively pulsating midsection intended to further limit the slippage at the proximal attachment site by reducing the peak value of the tugging force. This tugging force could be considered a direct result of the systolic pressure wave traveling through the arterial system. The invention—pulsating stent graft—expands in its midsection when the pressure wave reaches maximal value and temporarily accumulates some volume of blood, decreasing the tugging force.

DETAILED DESCRIPTION

Typically an intraluminal stent graft is comprised of a stent or a series of stents with an internal or external stent cover, or both, the said stent cover made of PTFE film or similar material. To accommodate for the change in the size of the artery the proximal end of the stent graft has a larger diameter than the distal end. Often the proximal end of the stent graft is also equipped with elements like hooks or an uncovered stent for attaching the body of the device to the arterial wall. Bifurcated versions of the stent graft would branch off to the vessels in the arterial tree.

Typically the stent graft tapers off in a uniform fashion from the larger proximal opening to the smaller distal opening. The cross-section of the lumen of the stent graft remains substantially circular throughout the length of the stent graft body within constrains allowed by the structural elements of the stent.

Figure 2:
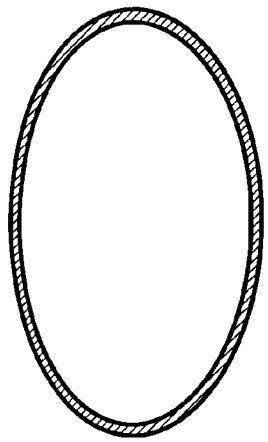
FIG. 2 shows the cross-section of the device along the plane marked on FIG. 1.
Figure 1:
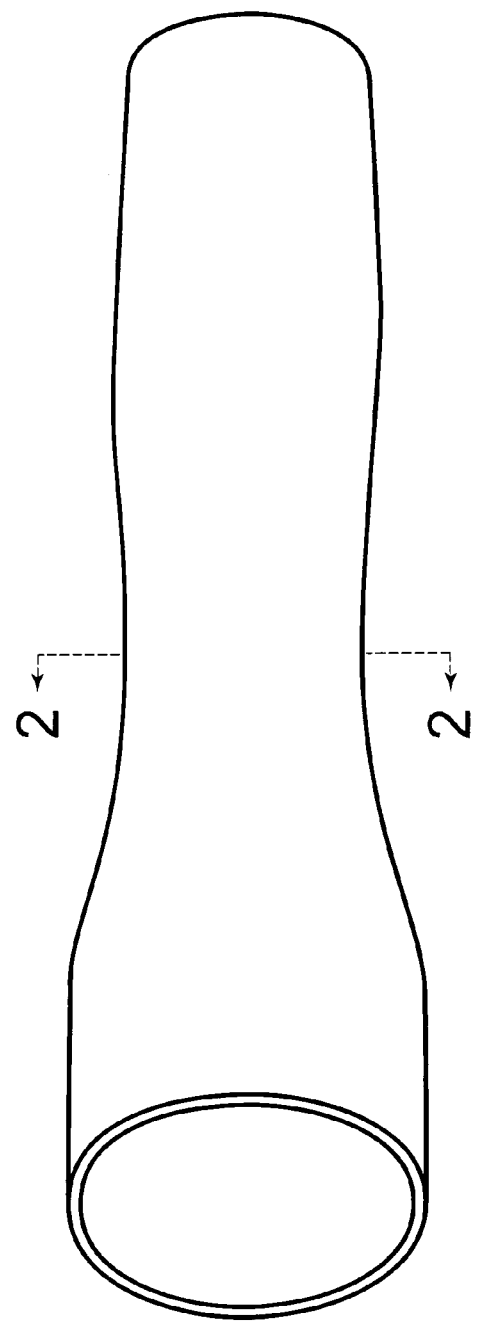
FIG. 1 shows the side view of the intraluminal device.

FIG. 1 and FIG. 2 describe an intraluminal stent graft with a midsection, which under diastolic blood pressure, with considerations made for the external pressures from the surrounding body fluids and tissues, becomes approximately elliptical with the area of the cross-section of its lumen decreasing by 10% or more compared with systolic blood pressure conditions, when the stent graft expands to a shape which has a cross-section that is as closely circular as allowed by the structural elements of the stent.

The same effect as described in the previous paragraph is obtained by implanting a stent, which has a noncircular cross-section of its lumen in a relaxed state, inside a previously implanted stent graft or graft.

One of the possible embodiments of the invention involves a stent graft consisting of a series of disconnected Z-stents as taught by Gianturco, U.S. Pat. No. 4,580,568, and covered by PTFE film. The diameter of the stent graft does not begin to taper off until its midsection, where the struts of one or more of the supporting Z-stents are more densely collected on two opposing sides of the graft resulting locally in a substantially elliptical cross-section of the lumen in the relaxed state.

The invention claimed is:

1. A tubular intraluminal stent graft comprising:
   a. a plurality of expandable stent portions, a midsection joined to said stent portions, and a lumen through said stent portions and said midsection,
   b. a stent cover portion covering openings in a wall aspect of said stent portions, and
   c. a proximal end and a distal end with circular cross-sections,
   wherein the midsection comprises a wall aspect located between said proximal and distal ends, the wall aspect of the midsection being configured to pulsate, wherein the midsection further comprises a transverse cross-section, when in a relaxed state, that is substantially more elliptical than a transverse cross-section proximal to said midsection which, when implanted into a large arterial vessel of human body, under systolic blood pressure, expands to a shape which has a maximally circular transverse cross-section as allowed by said stent portions of the stent graft, and which under diastolic blood pressure, relaxes to a shape that has an approximately elliptical transverse cross-section as allowed by said stent portions of the stent graft, with the major semi-axis of said approximately elliptical cross-section longer than its minor semi-axis and with the transverse cross-sectional area of the lumen decreased by 10% or more than under systolic blood pressure with considerations made for the pressure from the surrounding body fluids and tissues, and wherein the midsection, when expanded under systolic blood pressure, is configured to cause a reduction in a peak value of tugging force at the proximal end of the stent graft.

* * * * *